United States Patent [19]

Cammarata, III et al.

[11] Patent Number: 4,932,269

[45] Date of Patent: Jun. 12, 1990

[54] FLOW DEVICE WITH WATER TRAP

[75] Inventors: Frank Cammarata, III, Palatine; Jerry R. Grychowski, Lake Zurich; Robert Urman, Schaumburg; Alfred G. Brisson, Kildeer, all of Ill.

[73] Assignee: Monaghan Medical Corporation, Plattsburgh, N.Y.

[21] Appl. No.: 277,132

[22] Filed: Nov. 29, 1988

[51] Int. Cl.⁵ .......................... G01F 1/42; A61B 5/08
[52] U.S. Cl. .................................. 73/861.61; 128/725
[58] Field of Search ........... 73/861.52, 861.61, 861.62, 73/861.63, 861.64; 128/725

[56] References Cited

U.S. PATENT DOCUMENTS 2,760,371 8/1956 Borden ............................ 73/861.63
3,626,755 12/1971 Rudolph ........................... 73/861.52
3,949,739 9/1976 Rodder ................................. 128/725

Primary Examiner—Herbert Goldstein
Attorney, Agent, or Firm—Robert M. Wolters

[57] ABSTRACT

A flow device is provided for sensing air flow and includes a body having at the opposite ends thereof coaxial bores. Counterbores extend inwardly from the coaxial bores and are interconnected by a restricted bore having lateral bores extending from opposite ends thereof to provide a pneumatic pressure drop. The bottom portions of the respective counterbores are relieved to provide a pair of troughs for water collection outside of the normal air flow area so that water can accumulate for an extended period of time before interferring with pressure drop readings.

9 Claims, 1 Drawing Sheet

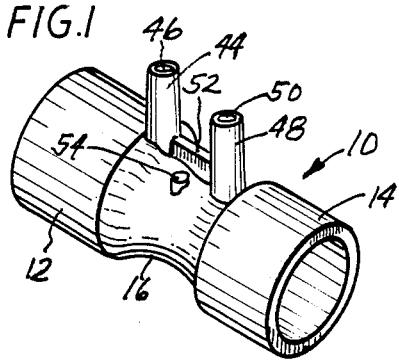
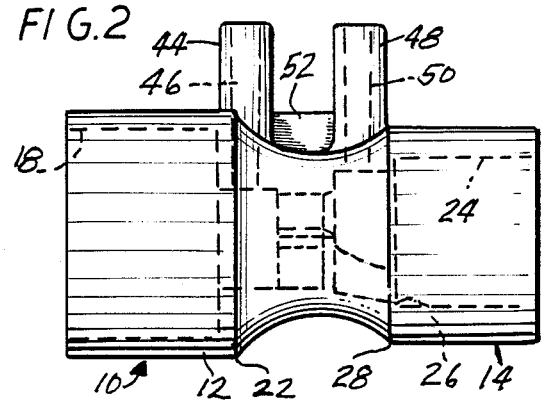
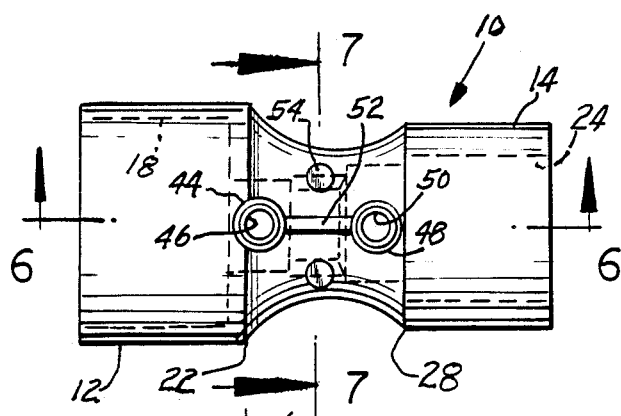
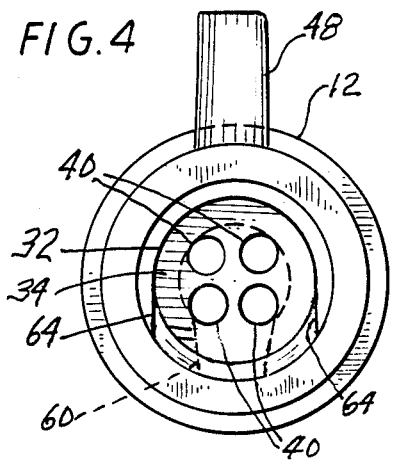
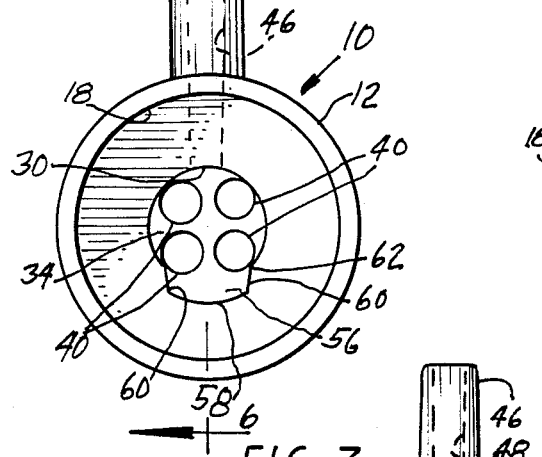
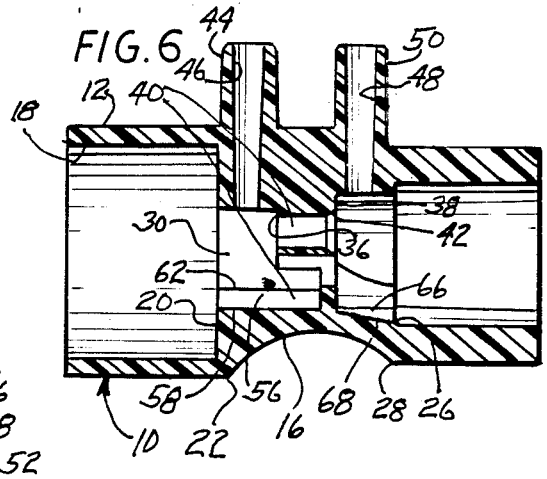
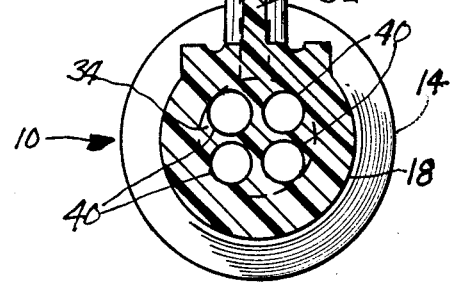

FLOW DEVICE WITH WATER TRAP

CROSS REFERENCE TO RELATED APPLICATION

The present application comprises an improvement over application Ser. No. 278,372, filed Dec. 1, 1988 for "Venturi Device for Sensing Air Flow" by Christopher Nowacki and Alfred G. Brisson. That application is assigned to the same assignee as the present application, namely Northgate Research, Inc. of Arlington Heights, Ill. The present application further is related to U.S. Design Pat. No. 296,530 by Christopher Nowacki and Alfred G. Brisson for "Design for Flow Sensor".

BACKGROUND OF THE INVENTION

Oxygen or a mixture of air and oxygen is often supplied to a patient in a hospital or nursing home. The oxygen can be supplied on a demand basis, or it can be used for forced or induced ventilation if the patient experiences difficulty in voluntary breathing. In any event, it is usually desired to monitor the volume and rate of flow of oxygen or other gas to the patient. Furthermore, it often is desired to measure the patient's capability of exhaling. The prior venturi devices for this purpose have been limited in operation and accuracy by accumulation of water condensed from the patient's exhaled breath. In such prior art venturi devices, enough water could accumulate in fifteen to thirty minutes to affect readings adversely.

OBJECTS AND SUMMARY OF THE PRESENT INVENTION

It is an object of the present invention to provide a Venturi device for sensing air flow in a rate volume monitor which incorporates structure for accommodating water accummulation.

More particularly, it is an object of the present invention to provide such a venturi device which has interior lower portions relieved for the storage of water.

In accordance with the present invention, a venturi device is provided which is generally similar to that in the aforesaid Nowacki and Brisson application "Venturi Device for Sensing Air Flow", but which has interior lower portions relieved to form miniature sumps for accummulation of water. The water accumulates out of the critical air flow area and does not change the readings for three to four hours, representing a significant improvement over the prior art.

THE DRAWINGS

The present invention will best be understood with reference to the following specification when taken in connection with the accompanying drawings wherein:

FIG. 1 is a perspective view of a venturi device constructed in accordance with the present invention;

FIG. 2 is a side view thereof on an enlarged scale;

FIG. 3 is a top view thereof;

FIG. 4 is an end view thereof as taken from the right end of FIG. 2;

FIG. 5 is an end view taken from the left end of FIG. 2;

FIG. 6 is a longitudinal sectional view thereof as taken along the line 6—6 in FIG. 3; and FIG. 7 is a transverse sectional view as taken substantially along the line 7—7 in FIG. 3.

DETAILED DISCLOSURE OF THE ILLUSTRATED EMBODIMENT

Turning now in greater particularity to the figures of the drawing, there will be seen a venturi device 10 for sensing air flow constructed in accordance with the principals of the present invention. The venturi device comprises a one piece molding of plastic resin material, preferably polycarbonate. The device may be of different sizes, but certain dimensions are given for a typical example. The device is provided with a cylindrical left or entering in portion 12 having an external diameter of 1.00 inch. The device further is provided with a right or exit end substantially cylindrical portion 14. At the right extremity of the portion 14 the outside diameter is 0.860, and there is a 1° taper so that the left margin of the right end portion 14 is of slightly greater margin that the right extremity thereof. The end portions 12 and 14 are connected by a central portion 16 that that is longitudinally articulate and provides a wasp-waisted appearance. The curve of the center portions 16 is on a radius of 0.477 inch, and the center of this radius of closer to the right end portion 14 than to the left end portion 12.

The left end cylindrical portion 12 is provided with a bore 18 having an entering diameter of 0.885 inch and tapering inwardly at 1° to a right angle shoulder 20 which is short of the outer extremity 22 of the left end portion where the outer cylindrical portion 12 forms a juncture with the central curved portion 16. The right end portion 14 is provided with a central bore 24 having an entering diameter of 0.608 inch and tapering inwardly at 1° to an internal shoulder 26. The internal shoulder is coincident with the left extremity 28 of the right end portion 14. The distance from the left extremity of the cylindrical portion to the internal shoulder 20, and also the internal dimension of the right end of the portion 14 to the internal shoulder 26 is 0.625 inch. The total overall length of the device from end to end if 2.000 inches.

The bores 18 and 24 are coaxial, and coaxial counterbores 30 and 32 extend respectively from these two bores toward one another. The right counterbore 32 is of 0.500 inch diameter while the left counterbore 30 is of 0.375 inch diameter, each tapering inwardly from its outer end very slightly to permit separation from mold parts. The total length from the shoulder 20 to the shoulder 26 is 0.625 inch.

Between the counterbores 30 and 32 there is provided a flow restriction comprising a barrier or wall 34 defined by flat faces 36 and 38 at the depths of the respective counterbores 30 and 32. The faces 36 and 38 are connected by four axially extending cylindrical bores 40 of 0.148 inch diameter, the right ends of which may be champferred at 42.

Each bore 18,24 is 0.625 inch long. The right counterbore 32 is 0.250 inch long, and the left counterbore 30 is 0.175 inch long. The wall 34 is 0.325 inch thick.

A first lateral tube 44 extends from the device 10 and has a bore 46 in fluid communication with the counterbore 30. The centerline of the bore is 0.750 inch from the left end of the device. The tube 44 is integral with the remainder of the device and connect thereto mostly in the center curve section 16, but partially overlying the left cylindrical portion 12. The tube extends 0.375 inch out from the circumference of the left cylindrical portion 12.

A second lateral tube 48 lies in a common axial plane with the tube 44 and has a bore 50 extending from the outer end into fluid communication with the counterbore 32. The centerline of the bore 50 is spaced 0.750 inch from the right end of the device and 0.500 inch from the centerline of the bore 46, and the two bores 46 and 50 are disposed nonsymetrically with respect to the flow restricting wall or barrier 34. It is intended in use that the lateral tubes 44 and 48 should extend substantially vertically upwardly as shown in the drawings for reasons that will appear hereinafter. The lateral tubes 44 and 48 are reinforced a longitudinally extending wall 52 extending between them and extending upwardly from the arcuate center section 16 of the device. Raised bosses 54 lie on either side of this wall. The tube 48 joins with the remainder of the device entirely within the curved center portion 16.

Both tubes 44 and 48 extend at right angles to the access of the device. Each has at its outer end an outer diameter of 0.1870 inch and tapers outwardly as it approaches the main body of the device. Each bore 46,50 at the outer end of the respective tube has a bore diameter of 0.094 inch with a very slight inward taper from the outer end to the inner end of the device to facilitate removal from molding tools. In use, the device 10 is inserted between two lengths of resilient tubing, such as rubber tubing. The tubing may be of the same diameter or different diameters. The supply tubing is connected to the left end 12 of the device, and is in turn connected to the usual Y-connector which supplies oxygen upon inhalation and which exhausts to the atmosphere upon exhalation. The supply tubing has an outside diameter slightly greater than the 0.870 diameter of the left portion bore 18, and can be pushed into this bore, wedging in place due to the taper of the bore. At the opposite end, the tubing going to the patient is connected to the smaller end 14 of the device. The tubing can be of the same diameter as the tubing at the left end, but stretched over the right end, stretching more tightly as it is pushed in over the taper thereof. It is common for the tubing feeding to the patient to be a smaller diameter, and in this instance, the outside diameter is such that the tubing can be wedged into the right portion bore 24. As will be understood, the tubing connected to the end 14 is in turn connected to an endotracheal tube inserted through the patient's mouth into the trachea. Air flow is to the right in the drawings upon inhalation, and is to the left upon exhalation.

Critical parts of the present invention are now to be disclosed, and include in FIGS. 5 and 6 a trough 56 formed as a downward extension of the counterbore 30 and having an arcuate floor 58 and a pair of upwardly extending walls 60. The floor 58 is arcuate as viewed from the end (FIG. 5) and is formed on a radius of 0.258 inch, with a 1° draft. The floor is straight in axial direction. The walls 60 taper upwardly and outwardly to join the counterbore 30 along lines 62. Each walls forms an angle of substantially 12.5° relative to the vertical.

Within the opposite end 14 the bottom portion of the counterbore 32 is flared outwardly at 64 (FIG. 4) to form a trough 66 having a curved bottom 68 forming a continuation of the bore 24.

During use, water, mostly from exhaled breath, will condense within the device 10, and this condensed water will collect in the troughs 58 and 66. A considerable time period of water collection has been found occur on the order of three to four hours, before the water interferes with air flow sufficiently to produce false readings of the electronic device connected by tubing to the lateral tubes 46 and 50. A pressure drop occurs across the barrier or wall 34 in accordance with the well known Bernoulli Principle, whereby upon inhalation the pressure in the lateral tubing bore 50 will be less than that in the bore 46, the condition being reversed upon exhalation. As will be understood, small diameter rubber or the like tubes are stretched over the tubes 44 and 48 and are connected to an air pressure-to-electric voltage transducer which is connected to further electronic equipment, for example, as in the prior U.S. Pat. No. 4,602,171, for calculating rate and volume of flow.

Thus, the relatively small troughs as just disclosed extend the usable reading period from as little 15 minutes up to three to four hours, whereby this very small change in structure makes an extensive functional change. The device can be removed after three to four hours when false readings may be expected, and thoroughly cleaned, dried and reinstalled.

The specific example of the invention as herein shown and described if for illustrative purposes only. Various changes in structure will no doubt occur to those skilled in the art, and will be understood as forming a part of the present invention insofar as they fall with the spirit and scope of the appended claims.

The invention is claimed as follows:

1. A flow device for sensing air flow comprising a body including first and second substantially cylindrical end portions and an intermediate center portion, said first and second end portions respectively having first and second outer diameters, said first and second end portions respectively having coaxial bores of respective first and second internal diameters, first and second counterbores in said intermediate center portion coaxial with and respectively having opposite open ends interconnecting with said first and second bores and respectively having first and second diameters smaller than either of said first and second internal diameters, means providing a flow restriction interconnecting said counterbores and comprising means providing axially directed bore means of small diameter relative to said counterbores, a pair of upstanding lateral bores through said intermediate portion and respectively in fluid communication with said counterbores on opposite sides of said small diameter bore means, and means providing a trough in at least one of said counterbores and extending below said one of said counterbores for collecting water condensed from air passing through said device and storing said water out of the air flow path through said device.

2. A flow device as set forth in claim 1 wherein a lower portion of said one of said counterbores is relieved downwardly to form said trough.

3. A flow device as set forth in claim 1 wherein said trough has a bottom wall substantially coincident with the corresponding bottom wall of the adjacent one of said coaxial bores.

4. A flow device as set forth in claim 1 and further including means providing two troughs, one in each counterbore.

5. A flow device as set forth in claim 2 and further including two troughs, one in each of said counterbores.

6. A flow device as set forth in claim 2 wherein said trough has a bottom wall substantially coincident with the corresponding bottom wall of the adjacent one of said coaxial bores.

7. A flow device as set forth in claim 2 wherein said trough has sidewalls tapering in toward one another from said one of said counterbores and tapering to a trough bottom wall.

8. A flow device as set forth in claim 2 wherein said trough has sidewalls tapering outwarding away from one another from one of said counterbores and extending to a trough bottom wall.

9. A flow device as set forth in claim 4 wherein one of said troughs has sidewalls tapering in toward one another from the respective counterbore to a trough bottom wall, and the other of said trough has sidewalls flaring outwardly away from one another to a trough bottom wall.

* * * * *